United States Patent [19]

Tarbit et al.

[11] Patent Number: 5,317,048

[45] Date of Patent: May 31, 1994

[54] ULTRA WHITE N,N'-ETHYLENE-BIS(TETRABROMOPHTHALIMIDE) AND ITS PRODUCTION IN ACETIC ACID

[75] Inventors: Brian Tarbit, Ashington; Brian Adger, Hexham; Paul Willett, Witton Le Wear, all of England

[73] Assignee: Great Lakes Chemical Corporation, W. Lafayette, Ind.

[21] Appl. No.: 954,281

[22] Filed: Sep. 30, 1992

[51] Int. Cl.$^5$ .................. C08K 5/3417; C07D 207/44
[52] U.S. Cl. ...................................... 524/94; 252/403; 548/462
[58] Field of Search .......................... 252/403; 524/94; 548/462

[56] References Cited

U.S. PATENT DOCUMENTS

| | | | |
|---|---|---|---|
| 3,868,388 | 2/1975 | Dotson, Jr. et al. | 548/462 |
| 4,087,441 | 5/1978 | Lee | 548/462 |
| 4,092,345 | 5/1978 | Wolford et al. | 252/8.1 |
| 4,125,535 | 11/1978 | Wolford | 548/462 |
| 4,374,220 | 2/1983 | Sonnenberg | 548/462 |
| 4,535,170 | 8/1985 | Sonnenberg | 548/462 |
| 4,644,066 | 2/1987 | Sonnenberg | 548/462 |
| 4,871,863 | 10/1989 | Khuddus | 548/462 |
| 4,873,341 | 10/1989 | Anderson | 548/462 |
| 4,894,187 | 1/1990 | Bonnet et al. | 252/609 |
| 4,914,212 | 4/1990 | Khuddus et al. | 548/461 |
| 4,990,626 | 2/1991 | Hutchinson et al. | 548/462 |
| 4,992,557 | 2/1991 | Hutchinson et al. | 548/462 |
| 5,049,601 | 9/1991 | Khuddus | 548/462 |
| 5,136,047 | 8/1992 | Khuddus et al. | 548/462 |

FOREIGN PATENT DOCUMENTS

| | | | |
|---|---|---|---|
| 0023420 | 7/1980 | European Pat. Off. | |
| 0195402 | 9/1986 | European Pat. Off. | 548/462 |
| 2926638 | 7/1979 | Fed. Rep. of Germany | |
| 3122668 | 5/1988 | Japan | 548/462 |

OTHER PUBLICATIONS

Spatz et al., "Some N-Substituted Tetrabromophthalimide Fire-Retardant Additives", Ind. Eng. Chem. Prod. Res. Develop., vol. 8, No. 4, pp. 397–398 (1969).

Primary Examiner—Kriellion S. Morgan
Attorney, Agent, or Firm—Woodard, Emhardt, Naughton, Moriarty & McNett

[57] ABSTRACT

Disclosed is a process for producing an ultra-white N,N'-ethylene-bis(tetrabromophthalimide) product useful as a flame retardant. Also disclosed is a flame retardant composition predominantly comprised of N,N'-ethylene-bis(tetrabromophthalimide) and having a yellowness index of about 4 or less.

28 Claims, No Drawings

ULTRA WHITE N,N'-ETHYLENE-BIS(TETRABROMOPHTHALIMIDE) AND ITS PRODUCTION IN ACETIC ACID

BACKGROUND

The present invention relates generally to fire retardants for use in polymer compositions and the like. More particularly, the present invention relates to an ultra-white N,N'-ethylene-bis-(tetrabromophthalimide) composition and to a method for its production.

Fire retardant compositions are performance chemicals that must meet exacting standards to gain acceptance and widespread use in industry. Among requirements for flame retardants, color is of particular importance. For a majority of applications, it is desired that the flame retardant be as white as possible. This enables production of high quality white plastics, but is also important because polymer processors require that colors of end products result from the particular pigment utilized rather than its combination with the color of the flame retardant.

One material receiving substantial attention as a flame retardant is N,N'-ethylene-bis-(tetrabromophthalimide) (EBT). However, acceptance of EBT compositions in industry has severely lagged largely because EBT compositions thus far available have been too yellow.

SUMMARY OF THE INVENTION

Accordingly, it is an object of this invention to provide a uniquely white EBT composition for use as a flame retardant.

Another object of the invention is to provide a method for producing a uniquely white EBT composition.

Another object of the invention is to provide a polymer composition and articles produced therefrom comprising the uniquely white EBT composition.

These and other objects of the invention are achieved by preferred embodiments of the present invention, one of which provides a process for preparing a highly white N,N'-ethylene-bis(tetrabromophthalimide) product. This process comprises reacting ethylene diamine and tetrabromophthalic anhydride in acetic acid to produce N,N'-ethylene-bis(tetrabromophthalimide). The N,N'-ethylene-bis(tetrabromophthalimide) is then recovered in a white precipitate, which is dried, so as to form a N,N'-ethylene-bis(tetrabromophthalimide) product with a yellowness index of about 4 or less. In a particularly preferred mode, this process is achieved by the steps of slurrying tetrabromophthalic anhydride into acetic acid, adding ethylene diamine to the slurry at a temperature of at least about 80° C. to form a reaction mixture, reacting the reaction mixture at a temperature of at least about 120° C. to achieve at least 70% conversion to N,N'-ethylene-bis(tetrabromophthalimide), recovering a precipitate from the reaction mixture including the N,N'-ethylene-bis(tetrabromophthalimide), and drying the precipitate to obtain a white particulate product predominantly comprised of N,N'-ethylene-bis(tetrabromophthalimide) and having a yellowness index of about 4 or less.

Another preferred embodiment of the invention relates to a flame retardant composition predominantly comprised of N,N'-ethylene-bis-(tetrabromophthalimide) and having a yellowness index of about 4 or less. EBT compositions of this embodiment also preferably have a whiteness index of about 70 or greater. Such EBT compositions have unprecedented color quality in combination with other advantageous features further described below.

Additional objects, features and advantages of the present invention will be apparent from the following description.

DESCRIPTION OF THE PREFERRED EMBODIMENT

For the purposes of promoting an understanding of the principles of the invention, reference will now be made to certain embodiments and specific language will be used to describe the same. It will nevertheless be understood that no limitation of the scope of the invention is thereby intended, such alterations, further modifications and applications of the principles of the invention as described herein being contemplated as would normally occur to one skilled in the art to which the invention relates.

As indicated, a feature of this invention is the production of a highly white N,N'-ethylene-bis(tetrabromophthalimide) product by reacting ethylene diamine and tetrabromophthalic anhydride in an acetic acid medium. It has been discovered that by conducting this reaction in an acetic acid medium, EBT products of unprecedented whiteness can be obtained.

In this regard, it will be understood that the acetic acid used as the reaction medium starting material is preferably of high purity. For example, the use of acetic acid of 99%+ purity is preferred, and such grades are commercially available from many sources. It is most preferred that the initial water content of the acetic acid be less than about 0.1% although this has not been found to be critical to obtain desirable processes and products of the present invention. In another aspect, the applicants have discovered that the presence of acetic anhydride in the acetic acid can lead to the formation of an impurity which adversely affects TGA's of the final product. Although the present invention is not limited by any theory, it is believed that this impurity is diacylated amidic acid, that is, amidic acid that has been acylated at each nitrogen. Based on this discovery it is highly advantageous to employ acetic acid having low acetic anhydride content, such as less than about 0.1%.

In another aspect of the invention, the acetic acid used for the reaction medium may be regenerated from the mother liquors of a previous synthesis, while still obtaining the uniquely white product. This can be accomplished by treating the mother liquors from a previous reaction with sufficient acetic anhydride to remove the water present. This acetic anhydride treatment is desirably conducted at a temperature of about 0°–150° C. Further, after this treatment, the liquors can be distilled before use in the subsequent reaction, although this has not proven to be necessary.

Tetrabromophthalic anhydride ("TBPA") suitable for use in the process of the invention is commercially available. Particle sizes ranging up to 1000 microns or more are suitable for use in the invention, although it is preferable to use micronized material with an average particle diameter of less than about 50 microns. Additionally, the acid number of the TBPA is desirably less that about 0.2 mg/g to prevent formation of impurities, for example those which may be related to salts of the ethylene diamine.

As known and as used herein, ethylene diamine ("EDA") refers to 1,2-diaminoethane. This material is also available from commercial sources, and for use in the present invention preferably assays at 99%+ purity. In particular, it is highly desirable that the ethylene diamine be free from water and carbonate.

As to specific synthesis details, it is preferred to first provide a slurry of tetrabromophthalic anhydride in the acetic acid medium. This slurry may be formed in the reaction vessel, or may be formed and then provided to the reaction vessel. As will be understood, the reaction vessel utilized will be able to withstand the pressure generated by the use of the acetic acid medium at the specified reaction temperatures.

The slurry is preheated to a temperature between about 80° and about 160° C., preferably about 90° to about 120° C., with agitation. This preheating can be for several hours or more but is preferably for a period up to about 1 hour. Thereafter, the EDA is added while the slurry remains at a temperature of about 80° to about 160° C., more preferably about 90° to about 120° C. The addition of EDA can be carried out over 1-2 hours or more, but is preferably carried out in less than about 10 minutes and more preferably less than about 5 minutes, for instance about 2 minutes or less. The addition of EDA, which is preferably in neat form but may also be in a suitable solvent (in small amounts to maintain the essentially acetic acid reaction medium sufficient to achieve the superior product color), is desirably achieved by blowing the EDA into the reaction vessel under pressure of an inert gas such as nitrogen to ensure a rapid addition and to ensure against hang-up in the lines. In this regard, it is of course important that the addition of EDA be carried out in such a manner that the momentary increase in pressure in the reaction vessel does not exceed the head pressure of the EDA addition system or the pressure limit of the particular operating system employed.

As will be understood, the EDA will be added in essentially stoichiometric amount (i.e. essentially a 1:2 molar ratio) with respect to the TBPA. That is, about 1 mole of EDA will be added for every 2 moles of TBPA in the slurry. It is important that this stoichiometric ratio be maintained since variations from it can lead to discolored product. For this reason, it is most preferable that the molar ratio of EDA to TBPA be kept in the range of 1:1.9 to 1:2.1. In highly advantageous reactions thus far, EDA to TBPA molar ratios of 1.01 to 2.00 have been employed while still acheiving 100% conversion of the TBPA to the amidic acid intermediate.

After EDA addition, the reaction is conducted at a temperature of about 110° to about 250° C., more preferably about 120° to about 180° C., with those temperatures above about 150° C. being most preferred. The water of reaction can but does not necessarily remain in the reaction mixture, which can be agitated using conventional and commercially available agitation systems. The reaction is continued at the reaction temperature preferably until at least about 70% conversion to the cyclized EBT product is obtained. In this regard it has been discovered that the termination of the reaction prior to achieving this 70% conversion results in substantial yellowing upon drying the precipitated material to achieve further cyclization and obtain the final dried product. For this reason it is even more preferred that the reaction be continued until conversion to the EBT product is essentially complete, e.g. at least 90% and more preferably at least 95% complete. Conversion to the cyclized EBT product can be determined, for instance, by observing the water event (which occurs upon cyclization of the amidic acid intermediate to form the EBT final product) by thermogravimetric analysis ("TGA"). In applicants' work, desirable reactions conducted at temperatures of about 160° to about 170° C. have been continued for periods in the range of 10 hours or more to essentially complete conversion to the cyclized EBT product, although this duration will of course vary in accordance with factors such as the temperature of reacting. The pressure of reacting has thus far been the autogenous pressure of the reaction mixture at the reaction temperature used, or slightly higher due to the pressurized nitrogen gas used during addition of the EDA. In runs with reaction temperatures of about 160°-170° C., reaction pressures of about 30 psi have been observed, although the pressure can be higher or lower and will of course vary with other reaction parameters.

After the reaction, the reaction mixture can be cooled to about 20° to about 100° C., more typically 80° to about 100° C., and the solids (typically up to about 40 weight % of the reacted medium and more preferably about 5% to about 30% of the reacted medium) can be isolated, e.g. by conventional centrifugation. The isolated product may then be washed, but it has advantageously been discovered that such washing is unnecessary to produce the high quality white products herein described. The isolated solid EBT composition is dried, preferably at elevated temperature, to remove acetic acid and to complete any residual cyclization to the EBT product. The drying and residual cyclization can be conducted at any temperature, but this step is preferably conducted at a temperature of at least about 175° C. and more typically at least about 200° C. The duration of the drying will vary in accordance with many factors such as the particular drying temperature used and the qualities of the EBT material being dried. The drying will in any event be of sufficient temperature and duration to essentially complete the residual cyclization to form a predominantly EBT product, which can be monitored by TGA. After this drying and completion of cyclization, a uniquely white EBT product is obtained, readily having a yellowness index of about 5 or less. In this regard, EBT products having yellowness indexes of about 4 or less, and even about 3 or less, are readily obtained without further purification or treatment. The EBT products typically have acid numbers of about 1 mg/g or less and more typically 0.5 mg/g or less. Bromine contents of the EBT products are usually at least about 65% and more usually about 65% to about 69%. Typical products also have melting point onsets above about 445° C., for instance usually in the range of about 460° C. and above.

The EBT product can be milled during and/or after the drying operations, for example as occurs in a Winkworth plough share type mixer. The dried product is then preferably micronized to provide an average particle diameter of about 5 microns or less, more preferably about 2 microns or less.

Another embodiment of the invention provides a flame retardant composition predominantly (i.e. about 95% or more) comprised of N,N'-ethylene-bis-(tetrabromophthalimide) and having a yellowness index of 4 or less. This composition may be produced for example by the process described above and more particularly detailed in the Examples below. In this regard, as will be understood, the "yellowness index" is determined in accordance with ASTM 1313 as can be measured by colormeter. EBT compositions of this embodiment also preferably have a "whiteness index" (ASTM 1313) of about 65 or greater, more preferably about 70 or greater, and advantageously are at least 98% comprised of the EBT product. Other preferred aspects of compositions of this embodiment are as set forth in the discussion of the first embodiment above and in the Examples which follow. The EBT compositions of the invention are of unprecedented color quality and represent a highly significant improvement over materials previously reported in the literature or commercially available.

The EBT product of the invention can be incorporated as a flame retardant in virtually any flammable material, natural or man-made, but will usually be incorporated in flammable synthetic polymers using conventional compounding techniques. For instance, the EBT product may be incorporated into crosslinked or non-crosslinked polymers of olefinic monomers, for example ethylene, propylene and butylene homopolymers or their copolymers with other polymerizable monomers; polymers of styrenic monomers, e.g. high-impact polystyrene and styrene copolymers; polyurethanes; polyamides; polyimides; polycarbonates; polyethers; acrylic resins; polyesters, e.g. poly(ethyleneterephthalate) and poly(butyleneterephthalate; epoxy resins; alkyd resins; phenolics; elastomers, for example butadiene/styrene copolymers and butadiene/acrylonitrile copolymers; terpolymers of acrylonitrile, butadiene and styrene; natural rubber; butyl rubber; polysiloxanes; wool; cellulose; polyvinylchlorides, etc.

As will be understood, the level of EBT product incorporated into the flammable material will vary widely in accordance with many factors such as the particular flammable material used, the application contemplated, other additives present, etc. Typically, the EBT will be incorporated at levels between about 1% and 50% of the total system weight, and more commonly between about 5% and 30% of the total system weight.

It will be understood that other conventional additives may also be incorporated into the flammable material. For example, the EBT product can be incorporated along with other flame retardant materials such as oxides of Group V elements, especially antimony oxides. Additional conventional additives may include antioxidants, antistatic agents, colorants, fibrous reinforcements, fillers, foaming/blowing agents, catalysts, heat stabilizers, impact modifiers, lubricants, plasticizers, processing aids, UV light stabilizers, crosslinking/curing agents, etc.

In order to promote a further appreciation and understanding of the present invention and its features and advantages, the following examples are provided. It will be understood that these examples are illustrative, and not limiting, of the invention. Percentages given herein are percentages by weight unless indicated otherwise. Color analyses in the Examples were performed with a Minolta Tricolorstimulus colorometer in accordance with ASTM 1313.

EXAMPLE 1

To a 1 l. glass autoclave fitted with overhead stirrer, vent, pressure gauge, temperature probe, pressurized addition funnel and with a heated oil jacket was added TBPA (150 g., 0.323 mole, 2 micron) and acetic acid (600 mls). The resulting slurry was heated to 110° C. and ethylene diamine (9.6 g., 0.16 mole) added using nitrogen pressure over 10 seconds. The slurry was then stirred at 110° C. for 30 minutes and then heated to 160° C. These conditions were held for 18 hours. The reaction was then cooled to 80° C. and filtered. The product was then dried at 200° C. on a fluid bed drier. A white product was obtained showing the following characteristics.

| | |
|---|---|
| 1% weight loss | 363° C. |
| 10% weight loss | 486° C. |
| Impurity level | 0.24% |
| Whiteness index | 77.0 |
| Yellowness index | 3.5 |
| Acid number | 0.02 |

EXAMPLE 2

To a 1 l. glass autoclave fitted with overhead stirrer, vent, pressure gauge, temperature probe, pressurized addition funnel and with a heated oil jacket was added TBPA (150 g., 0.323 mole, 2 micron) and acetic acid (600 mls.). The resulting slurry was heated to 102° C. and ethylene diamine (10.2 g., 0.171 mole) added using nitrogen pressure over 5 seconds. The reaction was then heated to 160° C. These conditions were held for 12 hours. The reaction was then cooled to 80° C. and filtered. The product was then oven dried at 200° C. A white product was obtained showing the following characteristics.

| | |
|---|---|
| 1% weight loss | 336° C. |
| 10% weight loss | 463° C. |
| Impurity level | 4.95% |
| Whiteness index | 77.9 |
| Yellowness index | 3.3 |
| Acid number | 0.09 |

EXAMPLE 3

To a 1 l. glass autoclave fitted with overhead stirrer, vent, pressure gauge, temperature probe, pressurized addition funnel and with a heated oil jacket was added TBPA (150 g., 0.323 mole, 2 micron) and acetic acid (600 mls). The resulting slurry was heated to 102° C. and ethylene diamine (10.6 g., 0.176 mole) added using nitrogen pressure over 5 seconds. The reaction was then heated to 160° C. These conditions were held for 12 hours. The reaction was then cooled to 80° C. and filtered. The product was then oven dried at 200° C. A white product was obtained exhibiting the following characteristics (n/d=not detectable).

| | |
|---|---|
| 1% weight loss | 328° C. |
| 10% weight loss | 450° C. |
| Impurity level | 4.98% |
| Whiteness index | 76.7 |
| Yellowness index | 2.9 |
| Acid number | n/d |

EXAMPLE 4

To a 1 l. glass autoclave fitted with overhead stirrer, vent, pressure gauge, temperature probe, pressurized addition funnel and with a heated oil jacket was added TBPA (150 g., 0.323 mole, 2 micron) and acetic acid (600 mls). The resulting slurry was heated to 102° C. and ethylene diamine (9.74 g., 0.1623 mole) added using nitrogen pressure over 5 seconds. The reaction was then heated to 160° C. These conditions were held for 12 hours. The reaction was then cooled to 80° C. and filtered. The product was then oven dried at 200° C. A white product was obtained showing the following characteristics.

| | |
|---|---|
| 1% weight loss | 341° C. |
| 10% weight loss | 482° C. |
| Impurity level | 0.616% |
| Whiteness index | 79.6 |
| Yellowness index | 3.2 |
| Acid number | 0.1 |

EXAMPLE 5

To a 1 l. glass autoclave fitted with overhead stirrer, vent, pressure gauge, temperature probe, pressurized addition funnel and with a heated oil jacket was added TBPA (150 g., 0.323 mol, 2 micron) and acetic acid (600 mls). The resulting slurry was heated to 102° C. and ethylene diamine (9.68 g., 0.1613 mole) added using nitrogen pressure over 5 seconds. The reaction was then heated to 160° C. These conditions were held for 12 hours. The reaction was then cooled to 80° C. and filtered. The product was then oven dried at 200° C. A white product was obtained showing the following characteristics.

| | |
|---|---|
| 1% weight loss | 341° C. |
| 10% weight loss | 484° C. |
| Impurity level | 0.8% |
| Whiteness index | 77.9 |
| Yellowness index | 2.7 |
| Acid number | 0.08 |

EXAMPLE 6

To a 1 l. glass autoclave fitted with overhead stirrer, vent, pressure gauge, temperature probe, pressurized addition funnel and with a heated oil jacket was added TBPA (150 g., 0.323 mole, 2 micron) and acetic acid (600 mls). The resulting slurry was heated to 160° C. and ethylene diamine (9.7 g., 0.161 mole) added using nitrogen pressure over 5 seconds. The reaction was then heated to 160° C. These conditions were held for 12 hours. The reaction was then cooled to 80° C. and filtered. The product was then dried on a fluid bed drier at 200° C. A white product was obtained showing the following characteristics.

| | |
|---|---|
| 1% weight loss | 267° C. |
| 10% weight loss | 362° C. |
| Impurity level | 2.03% |
| Whiteness index | 75.3 |
| Yellowness index | 3.8 |
| Acid number | n/d |

EXAMPLE 7

For comparative purposes, a process was performed using propionic acid instead of the acetic acid. As is shown, the process and its product are substantially inferior as compared to those of the invention. Accordingly, to a 1 l. glass autoclave fitted with overhead stirrer, vent, pressure gauge, temperature probe, pressurized addition funnel and with a heated oil jacket was added TBPA (150 g., 0.323 mole, 2 micron) and propionic acid (600 mls). The resulting slurry was heated to 105° C. and ethylene diamine (9.7 g., 0.161 mole) added using nitrogen pressure over 5 seconds. The reaction was then heated to 160° C. These conditions were held for 12 hours. The reaction was then cooled to 80° C. and filtered. The product was then dried on a fluid bed drier at 200° C. A white product was obtained showing the following characteristic.

| | |
|---|---|
| 1% weight loss | 325° C. |
| 10% weight loss | 472° C. |
| Impurity level | 4.40% |
| Whiteness index | 57.9 |
| Yellowness index | 9.2 |
| Acid number | 0.2 |

EXAMPLE 8

Another comparative run was made in propionic acid/xylene instead of acetic acid. Again, the results are highly inferior. Thus, to a 1 l. glass autoclave fitted with overhead stirrer, vent, pressure gauge, temperature probe, pressurized addition funnel and with a heated oil jacket was added TBPA (150 g., 0.323 mole, 2 micron), xylene (445 g.) and propionic acid (190 g.) The resulting slurry was heated to 98° C. and ethylene diamine (9.7 g., 0.161 mole) added using nitrogen pressure over 5 seconds. The reaction was then heated to 160° C. These conditions were held for 12 hours. The reaction was then cooled to 80° C. and filtered. The product was then oven dried at 200° C. A buff colored product was obtained showing the following characteristics.

| | |
|---|---|
| 1% weight loss | 378° C. |
| 10% weight loss | 484° C. |
| Impurity level | 0.11% |
| Whiteness index | 38.0 |
| Yellowness index | 16.5 |
| Acid number | 0.58 |

EXAMPLE 9

In several runs, it was demonstrated that the inventive process can be scaled up while achieving the high quality product of the invention, even having yellowness indexes in the range of about 2 to about 3 without further purification or treatment. Thus, to a 150 gallon glass lined vessel fitted with overhead stirrer (e.g. an Ekato Interprop Agitation Unit), vent, pressure gauge, temperature probe, pressurized addition funnel and with a heated jacket was added TBPA (106 kg, commercial grade) and acetic acid (360 kg). The resulting slurry was heated to 110° C. and ethylene diamine (6.92 kg) added using nitrogen pressure over 120 seconds. The reaction was then heated to 160° C. These conditions were held for 12 hours. The reaction was then cooled to 60° C. and filtered. The product was then oven dried at 200° C. A white product was obtained showing the following characteristics.

| | |
|---|---|
| 1% weight loss | 363° C. |
| 10% weight loss | 479° C. |
| Impurity level | 0.73% |
| Whiteness index | 77.1 |
| Yellowness index | 2.8 |
| Acid number | 0.30 |

EXAMPLE 10

To a 150 gall. glass lined vessel fitted with overhead stirrer, vent, pressure gauge, temperature probe, pressurized addition funnel and with a heated jacket was added TBPA (106 kg, 2 micron) and acetic acid (361 kg). The resulting slurry was heated to 110° C. and ethylene diamine (6.92 kg) added using nitrogen pressure over 120 seconds. The reaction was then heated to 150° C. These conditions were held for 14 hours. The reaction was then cooled to 60° C. and filtered. The product was then oven dried at 200° C. A white product was obtained showing the following characteristics.

| | |
|---|---|
| 1% weight loss | 361° C. |
| 10% weight loss | 487° C. |
| Impurity level | 0.40% |
| Whiteness index | 76.4 |
| Yellowness index | 2.4 |
| Acid number | 0.23 |

What is claimed is:

1. A process for preparing a highly white N,N'-ethylene-bis(tetrabromophthalimide) product, comprising:
    reacting ethylene diamine and tetrabromophthalic anhydride in acetic acid to produce N,N'-ethylene-bis(tetrabromophthalimide);
    recovering the N,N'-ethylene-bis(tetrabromophthalimide) in a white precipitate; and
    drying the precipitate, so as to form a N,N'-ethylene-bis(tetrabromophthalimide) product with a yellowness index of about 4 or less.

2. The process of claim 1 which includes the steps of:
    slurrying tetrabromophthalic anhydride into acetic acid;
    adding ethylene diamine to the slurry at a temperature of at least about 80° C. to form a reaction mixture;
    reacting the reaction mixture at a temperature of at least about 120° C. to achieve at least 70% conversion to N,N'-ethylene-bis(tetrabromophthalimide);
    recovering a precipitate from the reaction mixture including the N,N'-ethylene-bis(tetrabromophthalimide); and
    drying the precipitate to obtain a white particulate product predominantly comprised of N,N'-ethylene-bis(tetrabromophthalimide) and having a yellowness index of about 4 or less.

3. The process of claim 2 in which the addition of ethylene diamine is completed in about 10 minutes or less.

4. The process of claim 2 wherein the reacting is at a temperature of at least about 160° C.

5. The process of claim 2 wherein the drying is conducted at a temperature of at least about 175° C.

6. The process of claim 2 wherein the particulate product is at least 98% comprised of N,N'-ethylene-bis(tetrabromophthalimide).

7. The process of claim 2 wherein the molar ratio of tetrabromophthalic anhydride to ethylene diamine is in the range of 1.9:1 to 2.1:1.

8. The process of claim 2 including the step of micronizing the product.

9. The process of claim 2 wherein the product has a yellowness index of about 3 or less.

10. The process of claim 2 wherein the reacting is at a temperature of about 160° to about 170° C.

11. The process of claim 2 wherein the addition of ethylene diamine is conducted with the slurry at a temperature . of at least about 90° C.

12. A flame retardant composition predominantly comprised of N,N'-ethylene-bis(tetrabromophthalimide) and having a yellowness index of about 4 or less.

13. The product of claim 12 which has a yellowness index of about 3 or less.

14. The product of claim 13 which has a bromine content of at least about 65% by weight.

15. A polymer material comprising the product of claim 12.

16. A molded or extruded article formed from a polymer material according to claim 15.

17. A process for preparing a highly white N,N'-ethylene-bis(tetrabromophthalimide) product, comprising:
    (a) slurrying tetrabromophthalic anhydride into acetic acid;
    (b) adding ethylene diamine to the slurry thus obtained to achieve essentially a 1:2 molar ratio of ethylene diamine to tetrabromophthalic anhydride, said adding occurring with the slurry at a temperature of at least about 80° C.;
    (c) reacting the product of step (b) at a temperature of at least 120° C.; and
    (d) drying the product of step (c);
    so as to form a white product at least 95% comprised of N,N'-ethylene-bis(tetrabromophthalimide).

18. The process of claim 17 wherein the ethylene diamine is added over a time period not exceeding 10 minutes.

19. The process of claim 18 wherein the time period is about 5 minutes or less.

20. The process of claim 19 wherein the addition of ethylene diamine occurs with the slurry at a temperature of at least about 90° C.

21. The process of claim 20 wherein the product of step (b) is reacted at a temperature of at least 150° C.

22. The process of claim 21 wherein the product of step (b) is reacted at a temperature of about 160° C. to about 170° C.

23. The process of claim 22 wherein said reacting is sufficient to achieve at least 70% conversion to N,N'-ethylene-bis(tetrabromophthalimide).

24. The process of claim 23 wherein said reacting is sufficient to achieve at least 90% conversion to N,N'-ethylene-bis(tetrabromophthalimide).

25. The process of claim 24 wherein said reacting is continued for at least about 10 hours.

26. The process of claim 25 in which the drying is conducted at a temperature of at least about 175° C.

27. The process of claim 26 in which the product has a yellowness index of about 3 or less.

28. The process of claim 27 in which the product has a bromine content of at least about 65%.

* * * * *